(12) United States Patent
Eby et al.

(10) Patent No.: US 11,413,453 B2
(45) Date of Patent: Aug. 16, 2022

(54) BIOSTIMULATOR HAVING RESILIENT SCAFFOLD

(71) Applicant: Pacesetter, Inc., Sylmar, CA (US)

(72) Inventors: Thomas B. Eby, Mountain View, CA (US); Alex C. Soriano, Ventura, CA (US); Mark Carlson, Calabasas, CA (US)

(73) Assignee: PACESETTER, INC., Sylmar, CA (US)

( * ) Notice: Subject to any disclaimer, the term of this patent is extended or adjusted under 35 U.S.C. 154(b) by 0 days.

(21) Appl. No.: 16/791,785

(22) Filed: Feb. 14, 2020

(65) Prior Publication Data

US 2020/0261715 A1 Aug. 20, 2020

Related U.S. Application Data

(60) Provisional application No. 62/807,189, filed on Feb. 18, 2019.

(51) Int. Cl.
*A61N 1/37* (2006.01)
*A61N 1/05* (2006.01)
*A61N 1/375* (2006.01)
*A61N 1/378* (2006.01)

(52) U.S. Cl.
CPC ......... *A61N 1/0573* (2013.01); *A61N 1/3756* (2013.01); *A61N 1/3787* (2013.01); *A61N 1/37512* (2017.08); *A61N 2001/058* (2013.01)

(58) Field of Classification Search
CPC .............. A61N 1/0573; A61N 1/37512; A61N 1/3756; A61N 2001/058
See application file for complete search history.

(56) References Cited

U.S. PATENT DOCUMENTS

| | | | |
|---|---|---|---|
| 3,943,936 A | * | 3/1976 | Rasor ..................... A61N 1/056 607/35 |
| 4,796,643 A | * | 1/1989 | Nakazawa .............. A61N 1/057 600/375 |
| 9,272,155 B2 | | 3/2016 | Ostroff |
| 9,775,982 B2 | | 10/2017 | Grubac et al. |
| 10,022,538 B2 | | 7/2018 | Drasler et al. |
| 10,080,887 B2 | | 9/2018 | Schmidt et al. |
| 10,179,236 B2 | | 1/2019 | Haasl et al. |
| 10,449,354 B2 | | 10/2019 | Demmer et al. |
| 2007/0021664 A1 | | 1/2007 | Hettrick et al. |

(Continued)

*Primary Examiner* — Eric D. Bertram
(74) *Attorney, Agent, or Firm* — Womble Bond Dickinson (US) LLP (57) ABSTRACT

A biostimulator, such as a leadless cardiac pacemaker, including a fixation element and an electrode mounted on a resilient scaffold, is described. The fixation element and the resilient scaffold are coupled to a housing of the biostimulator. The resilient scaffold can support the electrode against a target tissue at a location that is radially offset from a location where the fixation element anchors the housing to the target tissue. A flexibility of the resilient scaffold allows the electrode to conform to a shape and movement of the target tissue when the housing is rigidly fixed to the target tissue by the fixation element. The resiliently supported electrode that is radially offset from the anchor point can reliably pace the target tissue without piercing the target tissue. Other embodiments are also described and claimed.

21 Claims, 9 Drawing Sheets

(56) References Cited

U.S. PATENT DOCUMENTS

| | | | |
|---|---|---|---|
| 2008/0255647 A1* | 10/2008 | Jensen | A61N 1/05 607/119 |
| 2009/0082828 A1* | 3/2009 | Ostroff | A61N 1/3756 607/36 |
| 2011/0238077 A1* | 9/2011 | Wenger | A61N 1/37512 606/129 |
| 2012/0109002 A1* | 5/2012 | Mothilal | A61B 5/0215 600/549 |
| 2012/0116489 A1* | 5/2012 | Khairkhahan | A61N 1/37518 607/127 |
| 2012/0172927 A1* | 7/2012 | Campbell | A61B 17/1215 606/213 |
| 2012/0197350 A1* | 8/2012 | Roberts | A61N 1/37205 607/60 |
| 2013/0116740 A1* | 5/2013 | Bornzin | A61N 1/3756 607/9 |
| 2015/0045868 A1* | 2/2015 | Bonner | A61N 1/37205 607/126 |
| 2015/0051612 A1* | 2/2015 | Schmidt | A61N 1/37205 606/129 |
| 2018/0126179 A1* | 5/2018 | Haasl | A61N 1/37512 |
| 2018/0207434 A1 | 7/2018 | Webb et al. | |
| 2018/0256902 A1 | 9/2018 | Toy et al. | |

* cited by examiner

BIOSTIMULATOR HAVING RESILIENT SCAFFOLD

This application claims the benefit of priority of U.S. Provisional Patent Application No. 62/807,189, filed Feb. 18, 2019, entitled "Biostimulator Having Resilient Scaffold," and that patent application is incorporated herein by reference in its entirety to provide continuity of disclosure.

BACKGROUND

Field

The present disclosure relates to biostimulators. More specifically, the present disclosure relates to leadless biostimulators.

Background Information

Cardiac pacing by an artificial pacemaker provides an electrical stimulation of the heart when its own natural pacemaker and/or conduction system fails to provide synchronized atrial and ventricular contractions at rates and intervals sufficient for a patient's health. Cardiac pacing by conventional pacemakers is usually performed by a pulse generator implanted subcutaneously or sub-muscularly in or near a patient's pectoral region, which delivers an electrical impulse to the heart via an elongated electrical lead implanted therein. Well known difficulties exist for conventional pacemakers, such as complex lead connectors and/or risks of mechanical failure of the leads. As a result, leadless cardiac pacemakers have been developed.

Leadless cardiac pacemakers are self-contained and self-sustainable biostimulators that can be attached to tissue within a dynamic environment. For example, leadless cardiac pacemakers can be implanted in chambers of the heart, which are soft, deformable, organic structures that have varying geometries. Dual chamber leadless pacing can include a first leadless cardiac pacemaker implanted in a ventricle and a second leadless cardiac pacemaker implanted in an atrium. The leadless cardiac pacemakers can include tissue anchors that project from a distal end of the pacemaker to engage a target tissue. The tissue anchors can hold a rigid electrode of the pacemaker against the tissue after implantation.

SUMMARY

A chamber of the heart, such as an atrium, can have pectinated tissue that can complicate the implantation of a leadless cardiac pacemaker. For example, the atrium can have a thin and corrugated topography that varies from patient to patient, and may prevent the implanted leadless cardiac pacemaker from successfully pacing the target tissue. More particularly, the shape and structure of the atrium can cause leadless cardiac pacemakers, which may otherwise function effectively in a ventricle, to exhibit inconsistent pacing thresholds. Even when the leadless cardiac pacemaker is successfully anchored, a thinness and/or rapid movement of the atrial wall can allow an electrode that is rigidly supported at a nose of the leadless cardiac pacemaker to be pulled through the stimulable tissue of the atrium or to bounce in and out of contact with the stimulable tissue as the heart beats. Such poor or intermittent contact between the electrode and the stimulable tissue can result in ineffective pacing. Furthermore, when the rigidly supported electrode is adjacent to the tissue anchor, scarring from the anchor site can impede the electrical impulse delivered by the electrode, and thus, the leadless cardiac pacemaker may not pace the target tissue effectively. Accordingly, improvements in the support and placement of the electrode can improve the efficacy of leadless cardiac pacemakers in difficult anatomies.

A biostimulator, e.g., a leadless cardiac pacemaker, having an electrode mounted on a resilient scaffold is described below. The resilient scaffold can support the electrode away from a fixation element that anchors in a target tissue. Accordingly, the biostimulator provides a flexible mechanical system that gently couples the electrode to soft, deformable, and variable organic structures, e.g., atrial walls, for optimal long-term pacing performance.

In an embodiment, a biostimulator includes a housing having an electronics compartment and a longitudinal axis. The electronics compartment contains a processor configured to stimulate a target tissue. A fixation element is coupled to the housing to attach the housing to the target tissue. The fixation element can be a helix mounted on a helix mount of a header assembly, and the helix can extend around the longitudinal axis to a piercing tip. Accordingly, the piercing tip can engage the target tissue and torque may be transmitted through the housing of the biostimulator to cause the fixation element to screw into and attach to the target tissue.

A resilient scaffold extends radially outward from the housing to a tissue contact region. In an undeployed state, e.g., when the resilient scaffold is not being acted upon by the target tissue, the tissue contact region of the scaffold can be distal to a distal end of the fixation element. By contrast, when the fixation element is attached to the target tissue, the tissue region surrounding the attachment point can press against the tissue contact region. The tissue contact region can yield to, and remain in contact with, the target tissue. An electrode can be mounted on the resilient scaffold at the tissue contact region where the target tissue presses against the resilient scaffold. Accordingly, the electrode can stimulate the target tissue.

The resilient scaffold may have any of several structures. By way of example, the resilient scaffold can include an elongated strut. The elongated strut can extend outward from the first end of the housing to a second end in free space. Alternatively, the elongated strut can include a loop extending between the first end and a second end at the housing. An apex of the loop may be between the first end and the second end, and may contact the target tissue during deployment. The loop may be one of several loops rotationally distributed about the longitudinal axis. In an embodiment, the resilient scaffold includes a braided structure that has a deformed state and a preset state. In the preset state, the braided structure can press against the target tissue. An anchor may be mounted on the resilient scaffold to hold the tissue contact region against the target tissue. Any of several electrodes mounted on the resilient scaffold may be independently activatable by the processor in the electronics compartment to stimulate the target tissue when the resilient scaffold is pressed against the target site.

The biostimulator can be a leadless cardiac pacemaker. In an embodiment, a leadless pacemaker system includes the leadless biostimulator and a catheter to deliver the biostimulator to the target site. A method of delivering the biostimulator is also described.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Embodiments describe a biostimulator having an electrode mounted on a resilient scaffold. The biostimulator may be a leadless cardiac pacemaker used to pace cardiac tissue. The biostimulator may, however, be used in other applications, such as deep brain stimulation. Thus, reference to the biostimulator as being a cardiac pacemaker is not limiting.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction along a central axis of a biostimulator. Similarly, "proximal" may indicate a second direction opposite to the first direction. Such terms are provided to establish relative frames of reference, however, and are not intended to limit the use or orientation of a biostimulator to a specific configuration described in the various embodiments below.

In an aspect, a biostimulator includes a resilient scaffold, and an electrode mounted on the resilient scaffold. The electrode can be mounted at a tissue contact region on the scaffold at a location that is radially separated from a central axis of the biostimulator. For example, the central axis can be a longitudinal axis of a housing of the biostimulator, which extends through a fixation element of the biostimulator. The fixation element can anchor into a target tissue, e.g., an atrial wall, to hold the biostimulator against the target tissue. The resilient scaffold can support and press the electrode against the target tissue radially away from the fixation element. The tissue contact region can be distal to a distal end of the fixation element when the resilient scaffold is in a preset state, and thus, the resilient scaffold can flex when pressure is applied to the electrode by the target tissue. This flexibility can allow the electrode to maintain contact with the moving atrial wall without piercing the atrial wall. The biostimulator can therefore both effectively anchor within target tissue exhibiting low mechanical strength, and effectively contact the electrically conductive target tissue with a pacing electrode.

Figure 1:
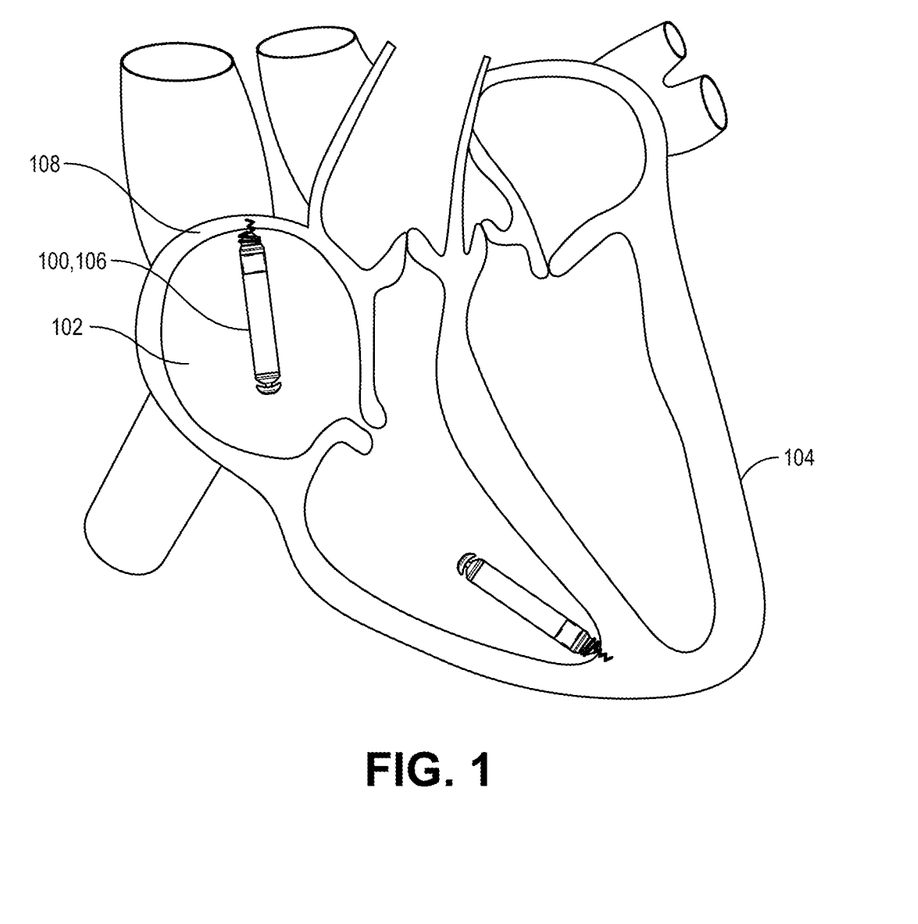
FIG. 1 is a pictorial view of a biostimulator implanted in a heart, in accordance with an embodiment.

Referring to FIG. 1, a pictorial view of a biostimulator implanted in a heart is shown in accordance with an embodiment. A pacing system includes one or more biostimulators 100. The pacing system can be a cardiac pacing system having a leadless biostimulator 100 in a chamber 102 of a heart 104. For example, the biostimulator(s) 100 can include one or more leadless cardiac pacemakers 106 in an atrium and/or a ventricle of heart 104. Each biostimulator 100 is suitable for placement on, or attachment to, an interior or exterior surface of chamber 102. For example, biostimulators 100 can attach to a target tissue 108 of chamber 102, e.g., an endocardium of the atrium.

Figure 2:
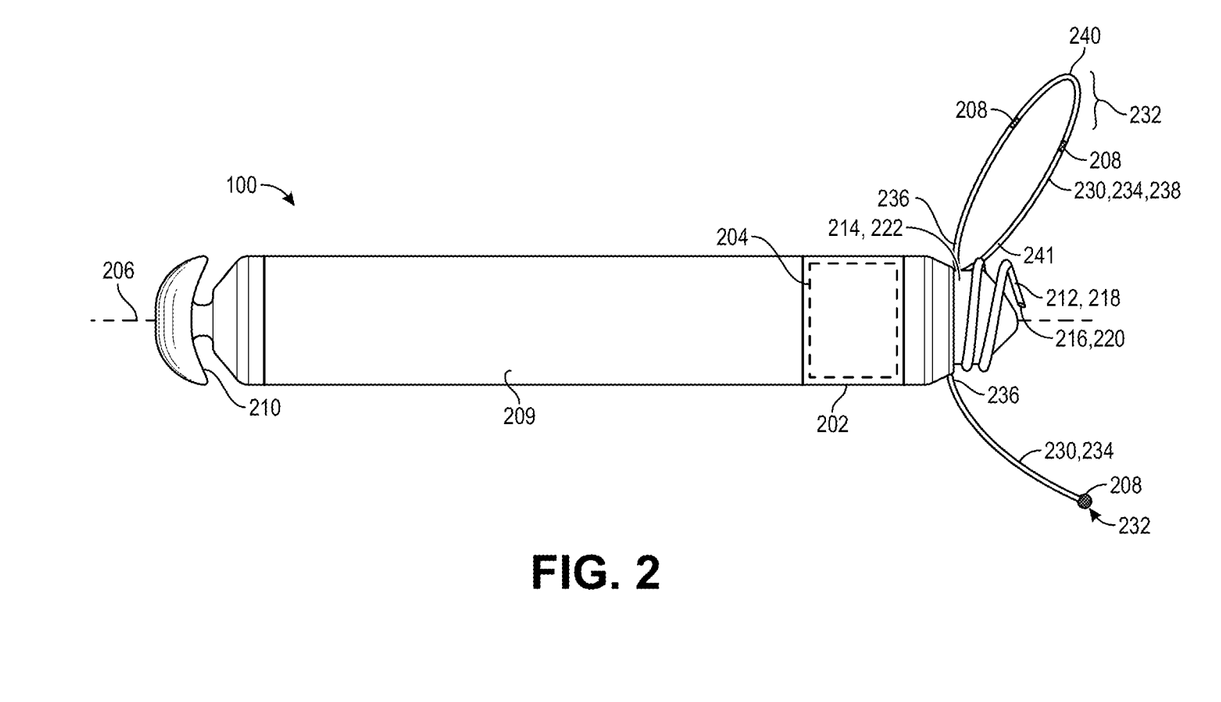
FIG. 2 is a side view of a biostimulator having an electrode mounted on a resilient scaffold, in accordance with an embodiment.

Referring to FIG. 2, a side view of a biostimulator having an electrode mounted on a resilient scaffold is shown in accordance with an embodiment. Biostimulator 100 can include a housing 202. Housing 202 can be a hermetically-sealed housing, and can include an electronics compartment 204. More particularly, electronics compartment 204 may be located within housing 202 along a longitudinal axis 206 of the housing 202, and can contain electronic components necessary for operation, e.g., sensing and/or pacing, of the biostimulator 100. In an embodiment, electronics compartment 204 contains a processor (not shown) configured to stimulate target tissue 108 via one or more electrodes 208. More particularly, the processor can control the generation of pacing impulses that are delivered through electrode(s) 208 to stimulate target tissue 108.

The hermetic housing 202 can be adapted to be implanted on or in a human heart 104, and can be cylindrical, rectangular, spherical, or have any other appropriate shape. Housing 202 can include a conductive, biocompatible, inert, and anodically safe material such as titanium, 316L stainless steel, or other similar materials. Biostimulator 100 can include an insulator, e.g., an insulating coating, disposed on the conductive material of housing 202 to separate the pacing electrode 208 (e.g., a cathode) from a return electrode 208 (e.g., an anode). For example, the insulator can include silicone, polyurethane, parylene, or another biocompatible electrical insulator commonly used for implantable medical devices. The return electrode 209 can be on a proximal portion of housing 202. More particularly, in an embodiment, the proximal electrode 209 is integral to housing 202. Alternatively, the proximal electrode 209 can be connected to housing 202 at a maximum distance of two centimeters from housing 202. In some embodiments, housing 202 itself can include an insulator, such as an alumina ceramic or other similar materials, instead of a conductor, and the one or more electrodes 208, 209 can be disposed upon housing 202. A low-polarization coating can be applied to the electrodes 208, 209, such as platinum, platinum-iridium, iridium, iridium-oxide, titanium-nitride, carbon, or other materials commonly used to reduce polarization effects.

Housing 202 can optionally contain an energy source (not shown) to provide power to the distal electrode 208. The energy source can be a battery, such as a lithium carbon monofluoride (CFx) cell, or a hybrid battery, such as a combined CFx and silver vanadium oxide (SVO/CFx) mixed-chemistry cell. Similarly, the energy source can be an ultracapacitor. In an embodiment, the energy source can be an energy harvesting device, such as a piezoelectric device that converts mechanical strain into electrical current or voltage. In certain embodiments, the piezoelectric energy harvester charges a rechargeable battery. In other embodiments, power generated by the piezoelectric energy source is stored in a super capacitor. In certain embodiments, the energy source is a combination of power technologies. For example, the power source may include a combination of a CFx battery and a piezoelectric device. In certain embodiments, the energy source can be located outside of housing 202. For example, the energy needed to power the electrical circuits could come from an ultrasound transducer and receiver, which receive ultrasound energy from an ultrasound transmitter located outside of housing 202.

In an embodiment, biostimulator 100 can have a torque transmission feature 210 that can be engaged by a delivery system to transmit torque to biostimulator 100. Torque transmission feature 210 can be an end cap placed on a proximal end of housing 202. In an embodiment, torque can be transmitted, at least in part, directly through the housing itself via a locking sleeve delivery system that relies on the housing surface area to transmit torque. Alternatively, torque transmission feature 210 can be incorporated directly in housing 202. For example, torque transmission feature 210 can include one or more slots, recesses, flats, or other surface features that can be engaged by the delivery system. In an embodiment, torque transmission feature 210 includes a pair of slots extending inward from an outer surface of housing 202. A lasso of the delivery system can be inserted into the slots to grip and retain biostimulator 100. While tension is applied to the lasso, the lasso or a catheter surrounding housing 202 and the lasso, can be rotated to transmit torque to biostimulator 100. The torque can cause rotation of housing 202, which can transmit torque to a fixation element 212 of biostimulator 100. In an embodiment, fixation element 212 is coupled to housing 202. For example, fixation element 212 may be a portion of a header assembly 214 that is mounted on housing 202. Fixation element 212 can have a distal end 216, which is distal to electronics compartment 204 contained within housing 202. Accordingly, distal end 216 of fixation element 212 can press against target tissue 108 when biostimulator 100 is advanced into chamber 102 of heart 104. When fixation element 212 is pressed against target tissue 108, fixation element 212 can anchor biostimulator 100 within target tissue 108. For example, when torque is transmitted to fixation element 212 via torque transmission feature 210, fixation element 212 can screw into target tissue 108, e.g., an endocardium and/or myocardium, to anchor therein.

In an embodiment, fixation element 212 includes a helix 218. For example, helix 218 can include a helically-formed wire extending around longitudinal axis 206 to a piercing tip 220 at distal end 216. Piercing tip 220 can have a sharpened point to pierce target tissue 108. Header assembly 214 may include a helix mount 222 having a threaded outer surface to receive helix 218. For example, a proximal end of helix 218 can engage the external thread of helix mount 222 and be screwed onto helix mount 222 to fasten helix 218 to housing 202. An adhesive can be used to bond helix 218 to helix mount 222 to further secure helix 218 to housing 202. Accordingly, helix 218 can be rigidly secured to housing 202 via helix mount 222. Other joining technologies, such as ultrasonic welding, along with joint designs common to such technologies, may be used to mate the components.

It will be appreciated that helix 218 is provided as a non-limiting example of fixation element 212 that can be used to secure housing 202 to target tissue 108. Other fixation mechanisms, such as hooks, barbs, adhesives, etc., may be incorporated at the distal end of housing 202 and/or on helix mount 222 to anchor biostimulator 100 to target tissue 108 at the target site. Furthermore, biostimulator 100 can include several fixation elements. For example, whereas a single helical fixation element 212 is illustrated in FIG. 2, biostimulator 100 can include additional fixation elements, e.g., additional helices, one or more barbs, etc.

Helix mount 222 can be removably mounted on housing 202. For example, a distal end of housing 202 containing electronics compartment 204 can have a threaded fastener that mates with a corresponding threaded fastener on helix mount 222. Accordingly, helix mount 222 can be screwed onto, and screwed off of, housing 202. Alternatively, housing 202 can be cut away from header assembly 214, e.g., using laser ablation to detach a proximal end of housing 202 from a distal end of housing 202. The detachable proximal section of biostimulator 100 can allow the biostimulator body containing the power source and/or electronic components to be removed from the anchored distal section of biostimulator 100. Accordingly, the biostimulator 100 body can be replaced by another biostimulator body having a new charged power source when the original power source is discharged.

In the case of a threaded attachment between header assembly 214 and the removable housing 202, torque can be transmitted through torque transmission feature 210 when fixation element 212 is anchored in target tissue 108 to cause housing 202 to disengage from helix mount 222. After removing housing 202 from helix mount 222 and from the patient, a new housing 202 can be introduced into the patient and engaged with helix mount 222 that remains fixed within target tissue 108. The new housing 202 can be threaded onto the original helix mount 222 by transmitting torque to the housing 202 via torque transmission feature 210. By following the process of removing a first housing and installing a second housing on header assembly 214 that is anchored to target tissue 108, a user can replace the power source used to drive active electrodes 208 of the header assembly 214, and thus, can increase a longevity of header assembly 214.

Header assembly 214 can include a resilient scaffold 230 and one or more electrodes 208. The one or more active electrodes 208 of biostimulator 100 can be mounted on resilient scaffold 230, which supports the electrodes 208 radially outward from longitudinal axis 206. Resilient scaffold 230 can be a framework that supports the electrodes 208 in a flexible, rather than a rigid, manner. A contrast between flexible support and rigid support can be described with respect to the capability of the electrodes 208 to move relative to housing 202. For example, when electrode 208 is mounted on housing 202, e.g., at a distal nose of header assembly 214 (FIG. 6), a force applied to electrode 208 will not cause relative movement between electrode 208 and housing 202. By contrast, electrodes 208 mounted on resilient scaffold 230 can move relative to housing 202 and/or fixation element 212 when a load is applied to them or to resilient scaffold 230.

In an embodiment, resilient scaffold 230 extends radially outward from housing 202 to a tissue contact region 232. Tissue contact region 232 may be distal to distal end 216 of fixation element 212. For example, in the preset state (undeformed or free) illustrated in FIG. 2, one or more of electrodes 208 are more distal than piercing tip 220 of helix 218. The flexibility of resilient scaffold 230 can allow electrodes 208 to move proximally as fixation element 212 is advanced to target tissue 108. More particularly, resilient scaffold 230 can bend backward under the pressure of the tissue surrounding the target site. Accordingly, fixation element 212 can be anchored in target tissue 108 while the resilience of the supporting framework allows electrodes 208 to yield and gently press against the surrounding tissue region.

Resilient scaffold 230 can have numerous configurations, several of which are described below. In an embodiment, resilient scaffold 230 includes an elongated strut 234. For example, resilient scaffold 230 illustrated below longitudinal axis 206 in FIG. 2 includes elongated strut 234 having a length of wire extending from a first end 236 at housing 202 to tissue contact region 232 radially outward from housing 202. The wire strut can terminate at tissue contact region 232, as shown, or the strut may include an atraumatic end curvature, such as a U-shaped tip, that curls proximally from tissue contact region 232. As shown, the atraumatic end may include a spherical or bulbous tip. In any case, elongated strut 234 can have a column strength that resists compression along an axis of the strut, however, elongated strut 234 may bend readily under loads applied at an angle to the strut axis. For example, elongated strut 234 can extend from first end 236 to electrode 208 at the strut terminus which is distal to piercing tip 220 in the direction of longitudinal axis 206, and a proximal reaction force applied to electrode 208 by target tissue 108 can cause elongated strut 234 to bend backward such that the electrode 208 shifts to a location that is proximal to piercing tip 220.

Resilient scaffold 230 can include one or more loop structures. For example, resilient scaffold 230 illustrated above longitudinal axis 206 in FIG. 2 includes elongated strut 234 having a loop 238 extending between first end 236 and a second end 241 at housing 202. Tissue contact region 232 on loop 238 can be a segment of loop 238 that presses against target tissue 108 during implantation. Loop 238 can extend substantially in a radial direction from housing 202 toward an apex 240. Apex 240 can be between first end 236 and second end 241. For example, apex 240 can be a location along the looped strut that has a minimum radius of curvature. Apex 240 may be a location that is farthest in a radial direction, relative to the longitudinal axis, along loop 238. Tissue contact region 232 can be adjacent to apex 240, e.g., a segment of loop 238 distal to apex 240. One or more electrodes 208 can be mounted on loop 238 at tissue contact region 232 to make contact with target tissue 108 when loop 238 is advanced to the target site. For example, loop 238 can extend from first end 236 to electrode 208 at tissue contact region 232 which is distal to piercing tip 220 in the direction of longitudinal axis 206. A proximal reaction force applied to electrode 208 by target tissue 108 can cause loop 238 to bend backward such that electrode 208 shifts to a location that is proximal to piercing tip 220.

Figure 3:
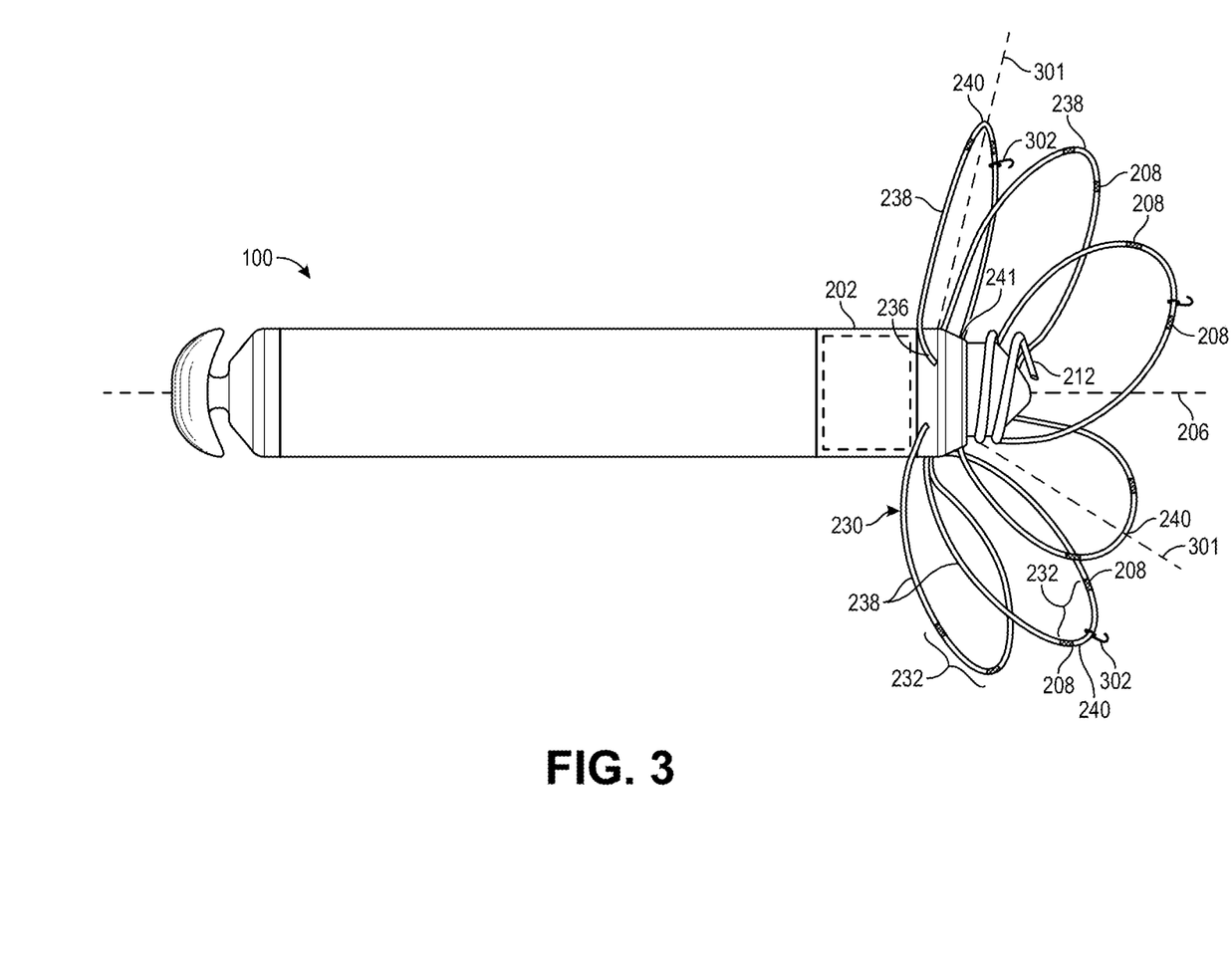
FIG. 3 is a side view of a biostimulator having an electrode mounted on a resilient scaffold having several loops, in accordance with an embodiment.

Referring to FIG. 3, a side view of a biostimulator having an electrode mounted on a resilient scaffold having several loops is shown in accordance with an embodiment. Loop 238 illustrated in FIG. 2 can be one of several loops 238 connected to housing 202. Loops 238 can be rotationally distributed about longitudinal axis 206. For example, biostimulator 100 can include three or more loops 238 that are sectors of a rotationally symmetric loop structure. The structure can be a radial structure in which each sector has a radial axis 301 extending from a point between first end 236 and second end 241 of each loop 238 through a respective apex 240 of the loop 238. In the case of the loop 238 structure having three loops 238, the radial axes 301 may be separated by an angle of about 120 degrees. It will be appreciated that the angle between radial axes 301 can increase when fewer loops 238 are present or decrease when more loops 238 are present. As described above, each loop 238 in the loop structure can have one or more electrodes 208 mounted along a respective tissue contact region 232.

Optionally, biostimulator 100 may include an anchor 302 mounted on resilient scaffold 230 at particular tissue contact region 232. For example, anchor 302 can be adjacent to one or more electrodes 208 on a respective loop 238. In an embodiment, anchor 302 is located along loop 238 between a pair of electrodes 208, e.g., at or near apex 240 of loop 238. Anchor 302 can be a thin wire wrapped around elongated strut 234 of loop 238. The thin wire may have a hook form, e.g., a form with an undercut, however, such form is provided by way of example and not limitation. In an embodiment, anchor 302 may be a barb extending distally from elongated strut 234. Anchor 302 may be a bump that increases friction without necessarily piercing tissue. For example, the bump may resist movement without causing trauma to the tissue, and thus, the bump can be readily removed or disengaged from the target tissue site as needed. In any case, anchor 302 can have a tip to engage target tissue 108 when resilient scaffold 230 is pressed against the target site. The anchor tip can grab the tissue to retain tissue contact region 232 of loop 238 against target tissue 108. Anchor 302 can anchor loop 238 at tissue contact region 232 radially away from a central location of biostimulator 100, e.g., longitudinal axis 206. Each anchor 302 can anchor into an endocardium of heart 104 to hold a nearby electrode 208 against the endocardium. Anchors 302 may have an anchor length that allows anchor 302 to grip endocardial tissue without piercing into the myocardium. Accordingly, anchors 302 may maintain contact between the active electrodes 208 and the stimulable tissue.

Resilient scaffolds 230 may be designed both geometrically and materially to resist plastic deformation. Hence a likelihood of fracture or yielding due to anatomical or interventional delivery and retrieval forces may be reduced. By way of example, nickel-titanium alloys (NiTi), which have fundamental shape memory and superelastic characteristics, may be used as a base material for scaffolds. To further enhance these material properties, NiTi tubing material may be formed into ribbons via laser-cutting to create scaffolding and anchor forms that harmoniously couple to the cardiac chamber 102. Alternatively, a host of bioabsorbable materials, e.g., mannitol, animal connective tissues, etc., may be crafted into scaffolding and anchors that provide time-dependent supports to the biostimulator 100.

Figure 4:
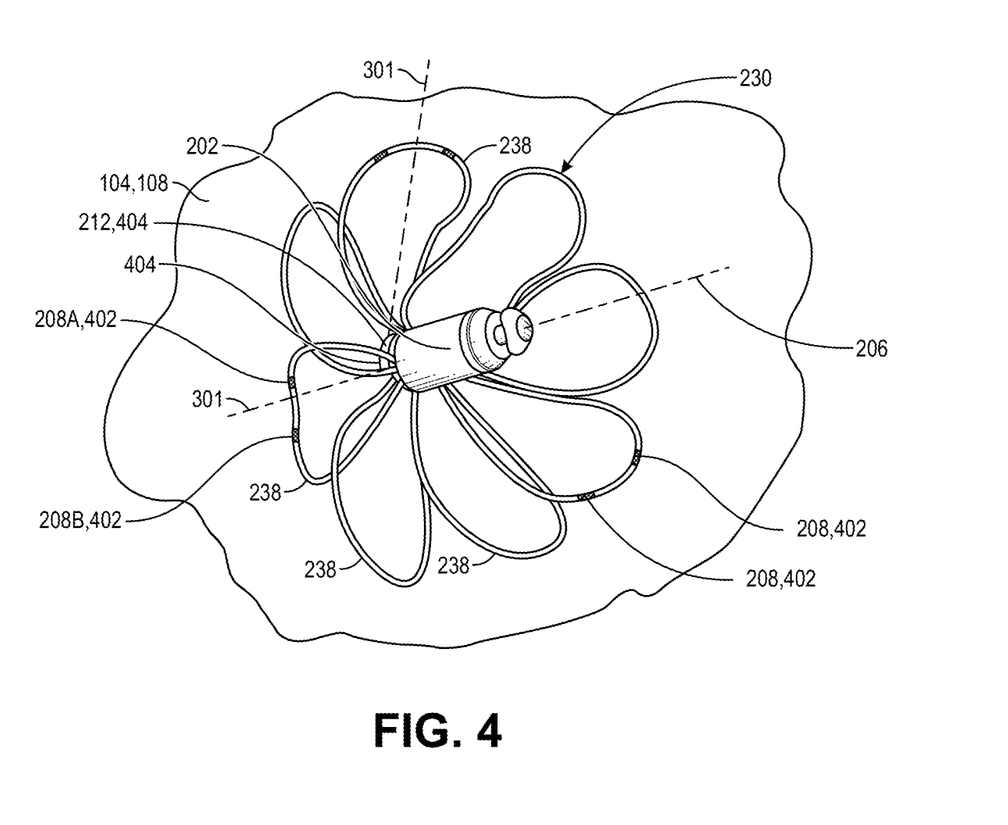
FIG. 4 is a perspective view of a biostimulator having an electrode mounted on a resilient scaffold implanted at a target site, in accordance with an embodiment.

Referring to FIG. 4, a perspective view of a biostimulator having an electrode mounted on a resilient scaffold implanted at a target site is shown in accordance with an embodiment. When biostimulator 100 is advanced toward target tissue 108, one or more electrodes 208 on a same or different loop 238 of the loop structure can contact target tissue 108. The location of contact between the electrodes 208 and target tissue 108 provide a stimulation point 402 that is radially separated from an anchor point 404 where fixation element 212 engages target tissue 108. Whereas fixation element 212 is rigidly attached to housing 202, electrodes 208 are able to move relative to housing 202 as heart 104 beats. More particularly, resilient scaffold 230 can flex, e.g., in a proximal direction, to conform to the chamber geometry. The resilience of the scaffold presses electrodes 208 against target tissue 108 without causing electrodes 208 to dig through endocardium into the myocardium. Resilient scaffold 230 can flex as the chamber 102 pulsates to maintain atraumatic contact between electrodes 208 and target tissue 108. Accordingly, housing 202 can be rigidly anchored in the endocardial and/or myocardial tissue of heart 104 while electrodes 208 are resiliently held against the stimulable endocardial tissue.

In an embodiment, electrodes 208 are independently activatable by the processor of biostimulator 100 to stimulate target tissue 108. The processor may be configured to detect contact between electrodes 208 and target tissue 108. For example, an electrical resistance between a pair of electrodes 208A, 208B on a respective loop 238 can be sensed and used to determine whether the respective loop 238 is in contact with target tissue 108. The processor can direct a pacing stimulus to one or more electrodes 208 that are determined to be in contact with target tissue 108. Accordingly, even when resilient scaffold 230 does not conform perfectly to target tissue 108 and some electrodes 208 do not have good contact with the underlying endocardium, at least one of electrodes 208 may be in contact with the endocardium, and thus, pacing of target tissue 108 may be consistently provided to heart 104 through the contacting electrode 208.

Figure 5:
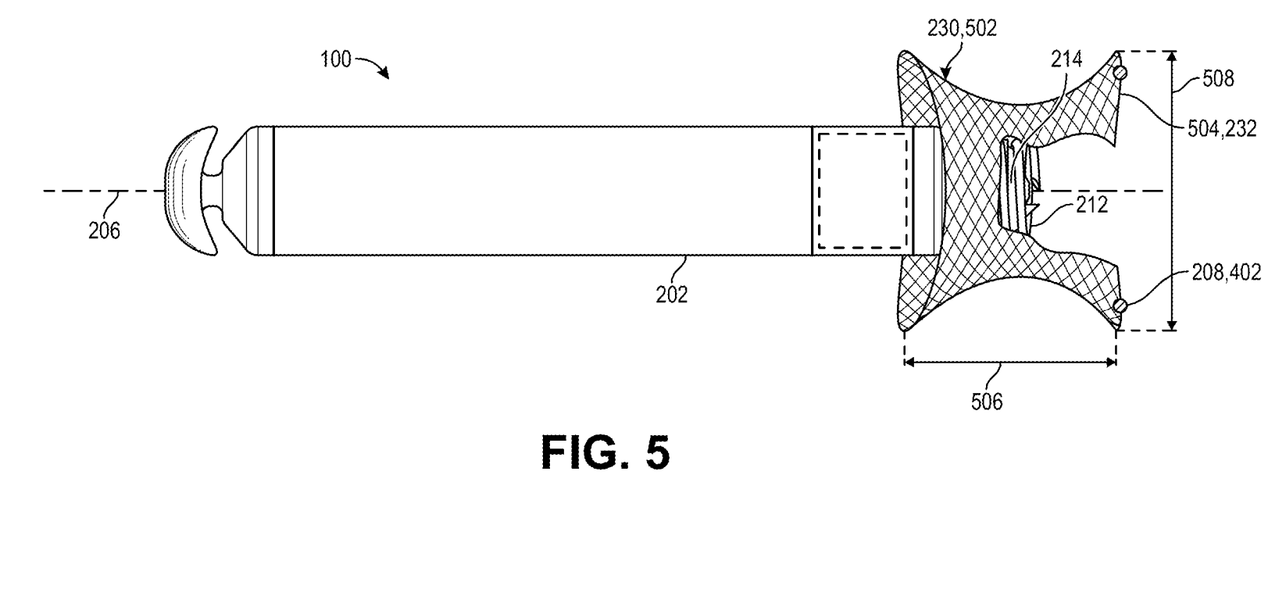
FIG. 5 is a side view of a biostimulator having an electrode mounted on a resilient scaffold having a braided structure, in accordance with an embodiment.

Referring to FIG. 5, a side view of a biostimulator having an electrode mounted on a resilient scaffold having a braided structure is shown in accordance with an embodiment. Resilient scaffold 230 can include a braided structure 502. Braided structure 502 can have several strands extending from a proximal connection point to a distal connection point on biostimulator 100. Connection points of the strands are not shown in FIG. 5, however, it will be appreciated by one skilled in the art that the connection points can be on header assembly 214 or housing 202 of biostimulator 100. The strands can extend radially outward from the connection points to form an interlacing pattern that has an outer surface. For example, the outer surface can have an hourglass shape. The shape of the outer surface may instead be toroidal, spherical, etc. The outer surface of braided structure 502 may have a distalmost lip 504 facing in the distal direction. The distalmost lip 504 may be opposite of a proximalmost lip 504. Lip 504 provides tissue contact region 232 of resilient scaffold 230 because as biostimulator 100 is advanced toward target tissue 108, lip 504 can press against target tissue 108 surrounding longitudinal axis 206.

In an embodiment, fixation element 212 is mounted on housing 202 around the longitudinal axis 206, and thus, lip 504 provides a contact region having one or more stimulation points 402 that surround anchor point 404 where fixation element 212 engages target tissue 108. More particularly, one or more electrodes 208 can be mounted on braided structure 502 along lip 504 to pace target tissue 108 at stimulation points 402 surrounding the anchor point 404. The circumferentially located stimulation points 402 can increase a distance from the primary anchor and primary stimulation site, thereby promoting pacing performance longevity due to preservation of stimulable tissue.

Figure 8:
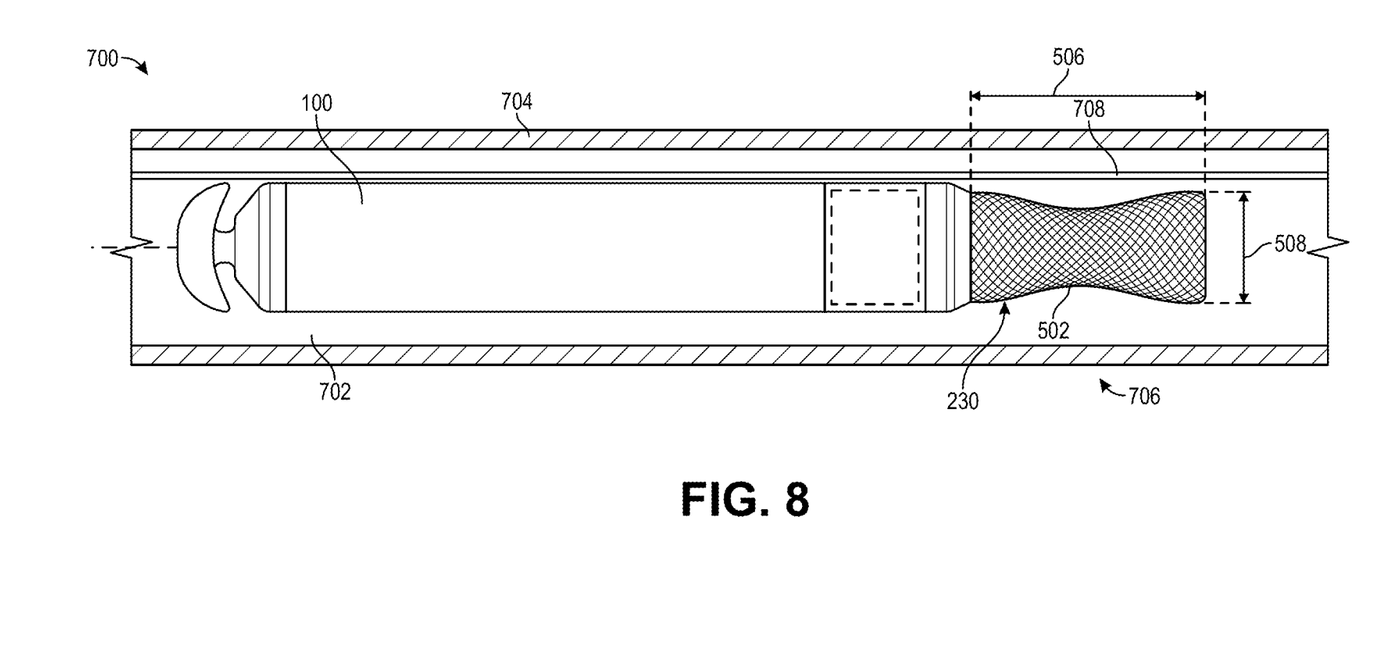
FIG. 8 is a side view of a biostimulator system including a biostimulator having a resilient scaffold that includes a braided structure loaded into a catheter, in accordance with an embodiment.

In an embodiment, resilient scaffold 230 is self-expandable. For example, braided structure 502 can have a preset state (FIG. 5) and a deformed state (FIG. 8). Elongated struts 234 of resilient scaffold 230, e.g., strands of braided structure 502, may be formed from a shape memory alloy such as NiTi. Accordingly, elongated struts 234 can be processed to have the first shape in a preset state, and can resiliently flex to the deformed state. By way of example, braided structure 502 can be stretched forward to have a first length 506 and a first width 508 in the deformed state (FIG. 8), however, when braided structure 502 is released it can recover to the preset state having a second length 506 and a second width 508. The second length 506 may be less than the first length 506 and the second width 508 may be greater than the first width 508, as illustrated. Alternatively, the second length 506 may be greater than the first length 506 and the second width 508 may be less than the first width 508, e.g., when braided structure 502 is released from a deformed pancake shape into a recovered cylindrical shape. In any case, the ability to recover or transition between the deformed state and the preset state is indicative of the natural resilience of braided structure 502. Accordingly, in the preset state, braided structure 502 can include electrodes 208 that are distal to fixation element 212, and thus, the electrode 208 can press against target tissue 108 when biostimulator 100 is implanted. As described above, as fixation element 212 engages and anchors into target tissue 108, resilient scaffold 230 can yield under the reaction load of target tissue 108 to cause electrodes 208 to move proximally relative to fixation element 212 and conform to the target site.

Figure 6:
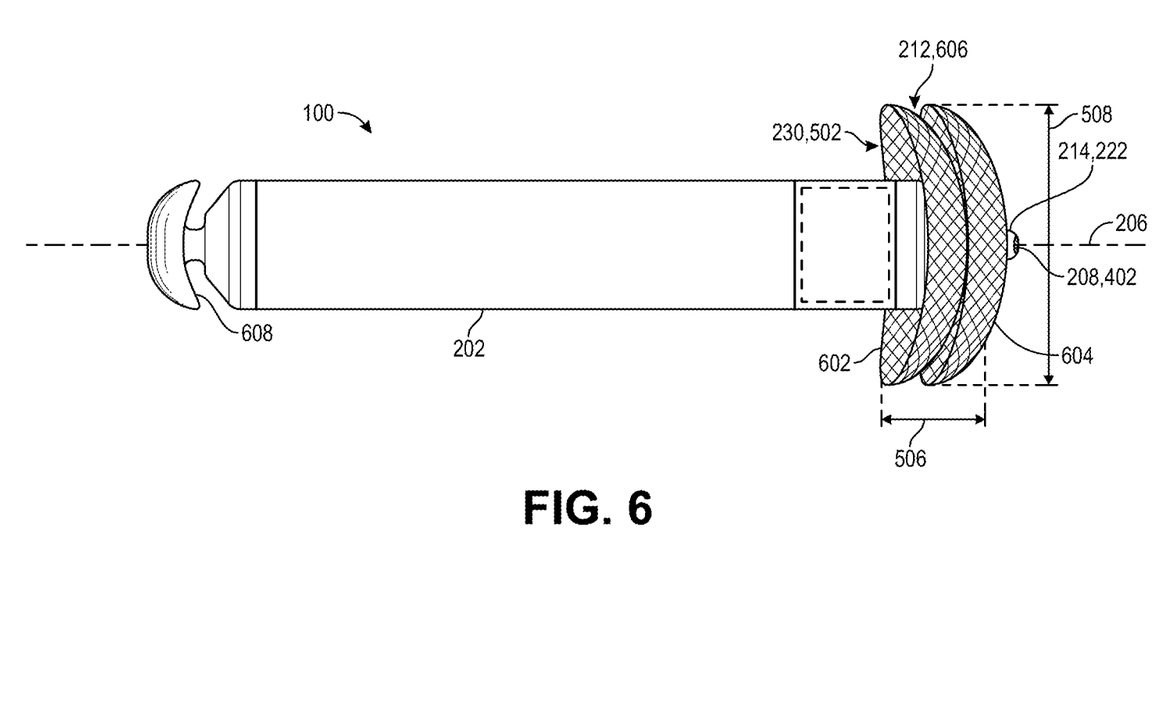
FIG. 6 is a side view of a biostimulator having a braided structure to anchor to tissue and an electrode on a housing, in accordance with an embodiment.

Referring to FIG. 6, a side view of a biostimulator having a braided structure to anchor to tissue and an electrode on a housing is shown in accordance with an embodiment. As described above, biostimulator 100 can include a central anchor and have electrodes 208 radially spaced outward from the anchor site. Alternatively, biostimulator 100 may include a central electrode 208 and have anchoring elements spaced radially outward from the stimulation site. For example, biostimulator 100 can include electrode 208 mounted on helix mount 222 of header assembly 214. Electrode 208 can be rigidly mounted on helix mount 222 such that relative movement between electrode 208 and housing 202 does not occur. Relative movement between electrode 208 and fixation element 212, however, may occur as described below.

In an embodiment, fixation element 212 may anchor against target tissue 108 without piercing the endocardial tissue of chamber 102. For example, fixation element 212 can anchor to tendinous cords within a chamber of heart 104, or within a transeptal opening, e.g., a patent foramen ovale, of heart 104. Resilient scaffold 230 can include braided structure 502 having a preset state in which a proximal disc 602 apposes a distal disc 604. Fixation element 212 can be formed by the space between the discs. For example, in the deformed state, braided structure 502 can be stretched such that the discs transition into tubular structures having outer surfaces that faced radially outward. When resilient scaffold 230 is released from the deformed state, braided structure 502 can recover to the preset state in which at least a portion of the outer surfaces of the discs face a longitudinal direction. For example, a distal face of proximal disc 602 can face distally, and a proximal face of distal disc 604 can face proximally. As braided structure 502 recovers, tendinous cords or a septal opening can be captured within a gap between the disc faces. Accordingly, the captured tissue can hold biostimulator 100 at the target site.

In the preset state, electrode 208 can be distal to a distalmost location on resilient scaffold 230. By way of example, a distal connection between the distal disc 604 and housing 202 or header assembly 214 may be proximal to the electrode 208 in the preset state. The captured tissue, e.g., the tendinous cords of chamber 102, are inward from the endocardial tissue of chamber 102, and thus, electrode 208 is located distal from the captured tissue in the preset state. More particularly, electrode 208 can press against the endocardial tissue when fixation element 212 atraumatically grips another tissue of heart 104.

Fixation element 212 can be anchored to tissue at a pinch point 606 that is radially outward, relative to longitudinal axis 208, from stimulation point 402. The resilience and flexibility of braided structure 502 can cause electrode 208 to be pressed forward against endocardial tissue without forcing electrode 208 through endocardial tissue. More particularly, electrode 208 can be biased against endocardial tissue and yet resilient scaffold 230 can allow electrode 208 to move proximally relative to pinch point 606 to yield under a reaction load exerted by heart 104. Accordingly, electrode 208 can conform to the stimulable tissue.

An advantage of the atraumatic fixation element 212 described above is the ability to retrieve the entire biostimulator 100 from the target site. Fixation element 212 can grip tissue near the target site by pinching or grabbing the tissue. Accordingly, the tissue can be released by relaxing or overcoming the grip. By way of example, a retrieval lasso can engage a retrieval feature 608 of biostimulator 100. Retrieval feature 608 may be a slot in housing 202, or another structure similar to that of torque transmission feature 210 described above. When the lasso is engaged with retrieval feature 608, a proximal load can be applied to the lasso to pull biostimulator 100 proximally. As biostimulator 100 moves proximally, resilient scaffold 230 can elongate and the gap at pinch point 606 can widen. When the gap widens, the captured tissue can be released and biostimulator 100 can therefore be retrieved under traction.

Figure 7:
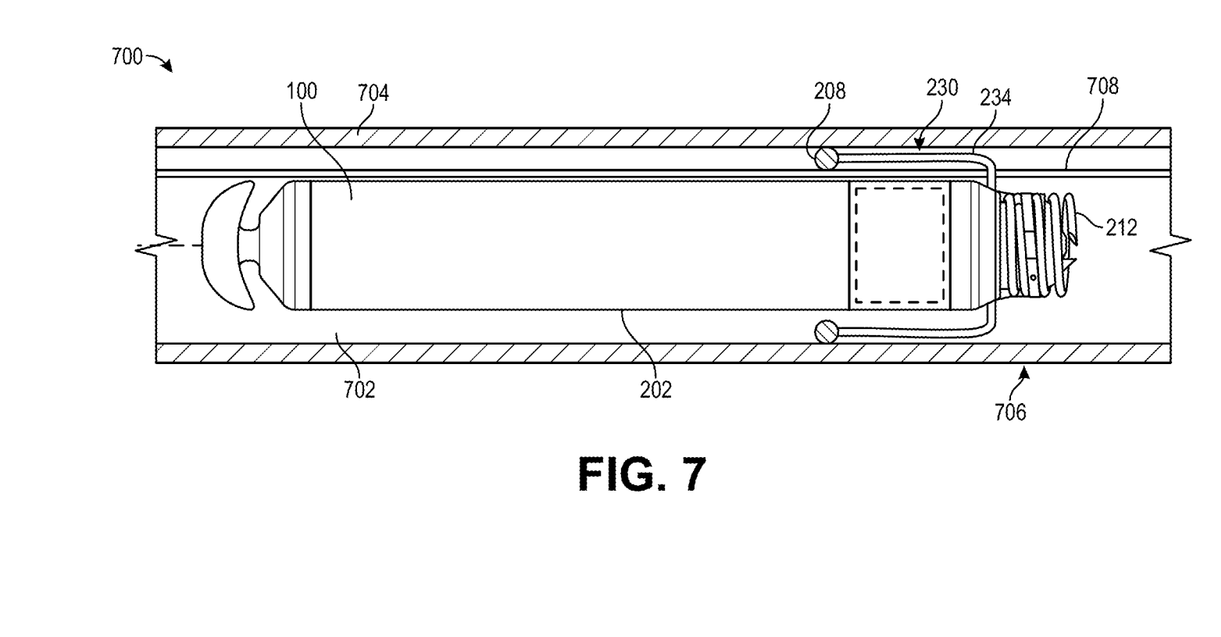
FIG. 7 is a side view of a biostimulator system including a biostimulator having a resilient scaffold loaded into a catheter, in accordance with an embodiment.

Referring to FIG. 7, a side view of a biostimulator system including a biostimulator having a resilient scaffold loaded into a catheter is shown in accordance with an embodiment. A biostimulator system 700 can be a leadless pacemaker system that includes leadless cardiac pacemaker 106 disposed in an inner lumen 702 of a catheter 704. Catheter 704 can include one or more flush ports at a proximal end (not shown) to allow a user to flush inner lumen 702 with a fluid, e.g., saline or therapeutic agent, during use.

Catheter 704 can include an elongated tubular structure surrounding inner lumen 702, and a distal region 706 of catheter 704 may include inner lumen 702 having a diameter of about 18 French, by way of example. Accordingly, inner lumen 702 can receive biostimulator 100 of approximately the same size. Inner lumen 702 may be slightly oversized relative to a diameter of housing 202 to provide an annular gap between biostimulator 100 and an inner surface of catheter 704. The annular gap can receive one or more components. For example, a guidewire 708 may be advanced through the annular gap to facilitate delivery of biostimulator system 700 as described below. Furthermore, resilient scaffold 230 can be folded back in a proximal direction relative to fixation element 212 and captured within the annular gap when biostimulator 100 is loaded into inner lumen 702. More particularly, when biostimulator 100 is loaded into catheter 704 such that resilient scaffold 230 is in the deformed state, elongated strut 234 and/or electrode 208 of resilient scaffold 230 can be proximal to fixation element 212. Accordingly, during delivery, fixation element 212 may be advanced from inner lumen 702 prior to the release of resilient scaffold 230. When deployed, resilient scaffold 230 can recover in the distal direction such that electrode 208 is distal to fixation element 212.

Referring to FIG. 8, a side view of a biostimulator system including a biostimulator having a resilient scaffold that includes a braided structure loaded into a catheter is shown in accordance with an embodiment. Like biostimulator 100 having elongated struts 234 or loops 238, biostimulator 100 having braided structure 502 can be loaded into distal region 706 of catheter 704 in the deformed state. Braided structure 502 can be stretched or elongated such that length 506 of resilient scaffold 230 is increased and width 508 is decreased to fit braided structure 502 within inner lumen 702. Braided structure 502 can be stretched over fixation element 212 (in the embodiment illustrated in FIG. 5) or electrode 208 (in the embodiment illustrated in FIG. 6). Accordingly, during delivery, resilient scaffold 230 may be advanced from inner lumen 702 and expand radially outward prior to release of a central fixation element 212 or electrode 208 from inner lumen 702. The resilience of resilient scaffold 230 can nonetheless allow the central component to be pressed forward into target tissue 108 to anchor within or stimulate the tissue at a location radially inward from tissue contact region 232 of resilient scaffold 230.

Figure 9:
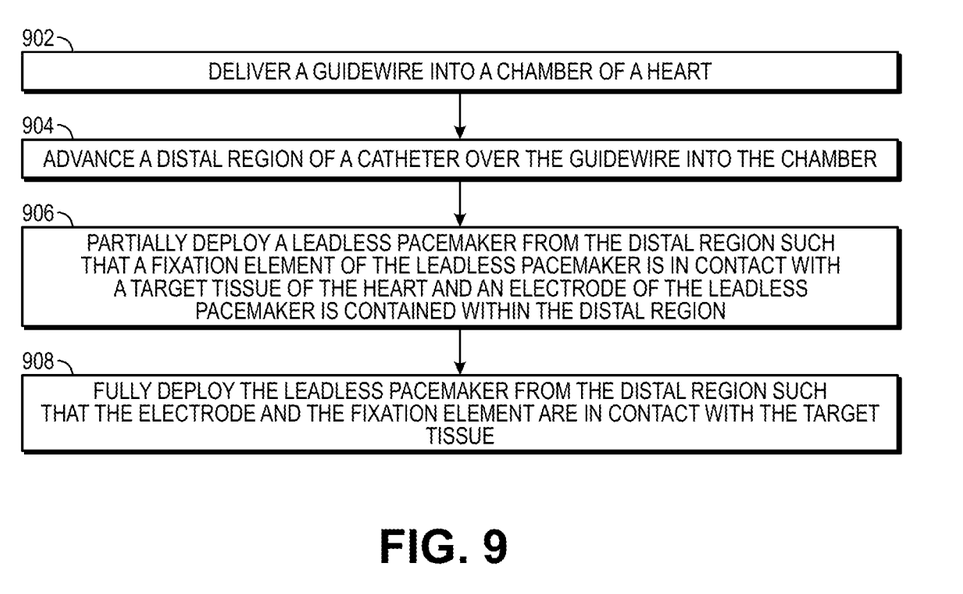
FIG. 9 is a flowchart of a method of implanting a biostimulator having an electrode mounted on a resilient scaffold at a target site, in accordance with an embodiment.

Referring to FIG. 9, a flowchart of a method of implanting a biostimulator having an electrode mounted on a resilient scaffold at a target site is shown in accordance with an embodiment. At operation 902, guidewire 708 is delivered into chamber 102 of heart 104. For example, guidewire 708 can be inserted into a patient intravenously and then navigated into heart 104 to the target site within an atrium.

Prior to or after delivery of guidewire 708, biostimulator 100 can be loaded into catheter 704. A proximal end of biostimulator 100 can be inserted into distal region 706 of catheter 704. Resilient scaffold 230 can be deformed in a proximal direction (FIG. 7) or a distal direction (FIG. 8), and inserted into distal region 706 along with the remainder of biostimulator 100, e.g., fixation element 212. It will be appreciated that a lasso or another torque transmission component (not shown) can be incorporated in catheter 704 and engaged with torque transmission feature 210 of biostimulator 100.

At operation 904, catheter 704 is delivered over a guidewire 708 into heart 104. Inner lumen 702 can be flushed with saline using flush ports of catheter 704. A proximal end of guidewire 708 can be loaded into inner lumen 702, and distal region 706 of catheter 704 can be advanced over guidewire 708. More particularly, guidewire 708 can be tracked through inner lumen 702 along a side of biostimulator 100. Distal region 706 containing biostimulator 100 can therefore track over guidewire 708 into chamber 102 having target tissue 108, e.g., the atrium. The distal end of catheter 704 can be located adjacent to target tissue 108 for deployment of biostimulator 100 to the target site.

At operation 906, biostimulator 100 is deployed partially from distal region 706 of catheter 704. For example, fixation element 212 can be advanced out of distal region 706 without fully deploying resilient scaffold 230 (FIG. 7) or resilient scaffold 230 can be advanced out of distal region 706 without deploying fixation element 212 (FIG. 8). A pusher rod (not shown) can be inserted into inner lumen 702 through a proximal port of catheter 704 and advanced until a distal end of the pusher rod contacts a proximal end of biostimulator 100. The pusher rod can be pressed forward to push biostimulator 100 out of catheter 704. In the case of FIG. 7, in a partially deployed state, fixation element 212 can be placed in contact with the target tissue 108 while electrode 208 is contained within distal region 706. By contrast, in the case of FIG. 8, electrode 208 can be placed in contact with the target tissue 108 while fixation element 212 is contained within distal region 706.

When leadless cardiac pacemaker 106 is partially deployed such that fixation element 212 is in contact with the target tissue 108, torque can be transmitted to biostimulator 100 to fasten housing 202 to the target tissue 108. For example, guidewire 708 can be retracted into inner lumen 702 proximal to fixation element 212, and a torque can be applied to catheter 704 by the user to cause the distal end of catheter 704 to rotate against the target tissue 108. Fixation element 212 can include a helix 218, and helix 218 can screw into tissue in the partially deployed state. Biostimulator 100 can therefore be anchored in target tissue 108 while housing 202 is at least partly contained within inner lumen 702.

Optionally, partial deployment of leadless cardiac pacemaker 106 at operation 906 may include touching the target tissue 108 with one or more electrodes 208 of biostimulator 100 prior to fully deploying fixation element 212. For example, leadless cardiac pacemaker 106 can be partially deployed from distal region 706 such that in the partially deployed state, electrodes 208 mounted on resilient scaffold 230 contact the target tissue 108 while fixation element 212 is contained within distal region 706. Deploying the electrodes 208 ahead of fixation element 212 can allow hot mapping or scouting of the target tissue 108 to be performed prior to engaging the tissue with fixation element 212. Accordingly, the target site can be monitored and located by moving the electrodes 208 along the tissue. When the target site is determined, the fixation element 212 can be deployed.

At operation 908, biostimulator 100 can be fully deployed from distal region 706. In the fully deployed state, fixation element 212 and electrode 208 are in contact with target tissue 108. For example, as elongated struts 234 or braided structure 502 advance from the end of catheter 704, resilient scaffold 230 can recover from the deformed state to the preset state in which electrodes 208 move in a distal direction (naturally set to be distal of distal end 216 of fixation element 212). In situ, electrodes 208 may not move fully to the preset state because resilient scaffold 230 may encounter the chamber wall beforehand. Accordingly, electrodes 208 can be pressed against target tissue 108, as shown in FIG. 4. Biostimulator 100 can therefore be anchored in target tissue 108 with electrodes 208 gently maintained against target tissue 108, and catheter 704 and guidewire 708 can be retrieved from the patient. The implanted biostimulator 100 can be activated to begin pacing target tissue 108.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A biostimulator, comprising:
a housing having an electronics compartment and a longitudinal axis, wherein the electronics compartment contains a processor configured to stimulate a target tissue;
a helical fixation element coupled to the housing and having a distal end distal to the electronics compartment;
a resilient scaffold including a loop extending radially outward and distally from the housing to a tissue contact region distal to the distal end of the helical fixation element; and
an electrode mounted on the resilient scaffold at the tissue contact region to stimulate the target tissue.

2. The biostimulator of claim 1 further comprising a header assembly removably mounted on the housing, wherein the header assembly includes the helical fixation element, the resilient scaffold, and the electrode.

3. The biostimulator of claim 2, wherein the helical fixation element includes a helix mounted on a helix mount of the header assembly, and wherein the helix extends around the longitudinal axis to a piercing tip at the distal end.

4. The biostimulator of claim 1, wherein the resilient scaffold includes an elongated strut extending from a first end at the housing to the tissue contact region.

5. The biostimulator of claim 4, wherein the elongated strut includes the loop extending between the first end and a second end at the housing, and wherein the loop includes an apex between the first end and the second end.

6. The biostimulator of claim 5, wherein the loop is one of a plurality of loops coupled to the housing and rotationally distributed about the longitudinal axis.

7. The biostimulator of claim 1 further comprising an anchor mounted on the resilient scaffold at the tissue contact region.

8. The biostimulator of claim 1, wherein the electrode is one of a plurality of electrodes mounted on the resilient scaffold, and wherein the plurality of electrodes are independently activatable by the processor in the electronics compartment to stimulate the target tissue.

9. The biostimulator of claim 1, wherein the biostimulator is a leadless cardiac pacemaker.

10. A biostimulator system, comprising:
a catheter having an inner lumen; and
a biostimulator disposed in the inner lumen, wherein the biostimulator includes
a housing having an electronics compartment and a longitudinal axis, wherein the electronics compartment contains a processor configured to stimulate a target tissue,
a helical fixation element coupled to the housing and having a distal end distal to the electronics compartment,
a resilient scaffold coupled to the housing, wherein the resilient scaffold includes a loop extending radially outward and distally from the housing to a tissue contact region distal to the distal end of the helical fixation element, and
an electrode mounted on the resilient scaffold at the tissue contact region to stimulate the target tissue.

11. The biostimulator system of claim 10, wherein the biostimulator further comprises a header assembly removably mounted on the housing, wherein the header assembly includes the helical fixation element, the resilient scaffold, and the electrode.

12. The biostimulator system of claim 10, wherein the resilient scaffold includes an elongated strut extending from a first end at the housing to the tissue contact region.

13. The biostimulator system of claim 12, wherein the elongated strut includes the loop extending between the first end and a second end at the housing, and wherein the loop includes an apex between the first end and the second end.

14. The biostimulator system of claim 13, wherein the loop is one of a plurality of loops coupled to the housing and rotationally distributed about the longitudinal axis.

15. The biostimulator system of claim 10 further comprising an anchor mounted on the resilient scaffold at the tissue contact region.

16. The biostimulator system of claim 10, wherein the electrode is one of a plurality of electrodes mounted on the resilient scaffold, and wherein the plurality of electrodes are independently activatable by the processor in the electronics compartment to stimulate the target tissue.

17. A method, comprising:
delivering a guidewire into a chamber of a heart having a target tissue;
advancing a distal region of a catheter into the chamber of the heart, wherein the distal region has an inner lumen containing a biostimulator, and wherein the biostimulator includes a housing having an electronics compartment and a longitudinal axis, wherein the electronics compartment contains a processor configured to stimulate the target tissue, a helical fixation element coupled to the housing and having a distal end distal to the electronics compartment, a resilient scaffold including a loop extending radially outward and distally from the housing to a tissue contact region distal to the distal end of the helical fixation element, and an electrode mounted on the loop of the resilient scaffold at the tissue contact region to stimulate the target tissue; and
deploying the biostimulator from the distal region, wherein in a fully deployed state the electrode and the helical fixation element are in contact with the target tissue of the chamber of the heart.

18. The method of claim 17 further comprising partially deploying the biostimulator from the distal region, wherein in a partially deployed state the helical fixation element is in contact with the target tissue and the electrode is contained within the distal region.

19. The method of claim 17 further comprising partially deploying the biostimulator from the distal region, wherein in a partially deployed state the electrode is in contact with the target tissue and the helical fixation element is contained within the distal region.

20. A biostimulator, comprising:
a housing having an electronics compartment and a longitudinal axis, wherein the electronics compartment contains a processor configured to stimulate a target tissue;
a header assembly mounted on the housing;
a helical fixation element coupled to the housing and having a distal end distal to the electronics compartment;
a resilient scaffold including a braided structure having a plurality of strands extending radially outward and distally from the header assembly to a tissue contact region distal to the distal end of the helical fixation element, wherein the braided structure is self-expandable from a deformed state to a preset state, wherein the braided structure has a first length and a first width in the deformed state, and wherein the braided structure has a second length less than the first length and a second width greater than the first width in the preset state; and
an electrode mounted on the resilient scaffold at the tissue contact region to stimulate the target tissue.

21. A biostimulator system, comprising:
a catheter having an inner lumen; and
a biostimulator disposed in the inner lumen, wherein the biostimulator includes
a housing having an electronics compartment and a longitudinal axis, wherein the electronics compartment contains a processor configured to stimulate a target tissue,
a header assembly mounted on the housing,
a helical fixation element coupled to the housing and having a distal end distal to the electronics compartment,
a resilient scaffold including a braided structure having a plurality of strands coupled to the header assembly, wherein the plurality of strands extend radially outward and distally from the header assembly to a tissue contact region distal to the distal end of the helical fixation element, wherein the braided structure is self-expandable from a deformed state to a preset state, wherein the braided structure has a first length and a first width in the deformed state, and wherein the braided structure has a second length less than the first length and a second width greater than the first width in the preset state, and
an electrode mounted on the resilient scaffold at the tissue contact region to stimulate the target tissue.

\* \* \* \* \*